United States Patent
Montgomery et al.

(10) Patent No.: US 10,194,870 B2
(45) Date of Patent: *Feb. 5, 2019

(54) SYSTEMS AND METHODS FOR OPTIMIZING AUTOREGULATION MEASUREMENTS

(71) Applicant: COVIDIEN LP, Mansfield, MA (US)

(72) Inventors: Dean Montgomery, Edinburgh (GB); Paul S. Addison, Edinburgh (GB)

(73) Assignee: Covidien LP, Mansfield, MA (US)

( * ) Notice: Subject to any disclaimer, the term of this patent is extended or adjusted under 35 U.S.C. 154(b) by 225 days.

This patent is subject to a terminal disclaimer.

(21) Appl. No.: 15/146,548

(22) Filed: May 4, 2016

(65) Prior Publication Data
US 2016/0345913 A1 Dec. 1, 2016

Related U.S. Application Data

(60) Provisional application No. 62/166,973, filed on May 27, 2015.

(51) Int. Cl.
*A61B 5/02* (2006.01)
*A61B 5/00* (2006.01)
(Continued)

(52) U.S. Cl.
CPC .......... *A61B 5/7275* (2013.01); *A61B 5/0205* (2013.01); *A61B 5/14553* (2013.01); *G06F 19/00* (2013.01)

(58) Field of Classification Search
CPC .............. A61B 5/02028; A61B 5/0205; A61B 5/14551
See application file for complete search history.

(56) References Cited

U.S. PATENT DOCUMENTS 4,776,339 A 10/1988 Schreiber
5,351,685 A 10/1994 Potratz
(Continued)

FOREIGN PATENT DOCUMENTS

EP 615723 A1 9/1994
WO WO9843071 A1 10/1998
(Continued)

OTHER PUBLICATIONS

Addison, P. S., et al.; "Low-Oscillation Complex Wavelets," Journal of Sound and Vibration, 2002, vol. 254, Elsevier Science Ltd., pp. 1-30.

(Continued)

*Primary Examiner* — Eric D. Bertram
(74) *Attorney, Agent, or Firm* — Shumaker & Sieffert, P.A.

(57) ABSTRACT

A method for monitoring autoregulation includes receiving a blood pressure signal and a regional oxygen saturation signal from a patient. The method also includes determining one or more pairs of linear correlation lines between the blood pressure signal and the regional oxygen saturation signal based on one or more bins. Each of the one or more bins includes one or more regional oxygen saturation values derived from the regional oxygen saturation signal. The method also includes determining a value indicative of the patient's autoregulation status based on a first pair of linear correlation lines selected from the one or more pairs of linear correlation lines and providing a signal indicative of the patient's autoregulation status to an output device.

21 Claims, 5 Drawing Sheets

(51) Int. Cl.
   *A61B 5/0205*  (2006.01)
   *A61B 5/1455*  (2006.01)
   *G06F 19/00*   (2018.01)

(56) References Cited

U.S. PATENT DOCUMENTS

| | | | |
|---|---|---|---|
| 5,482,034 | A | 1/1996 | Lewis et al. |
| 5,533,507 | A | 7/1996 | Potratz |
| 5,577,500 | A | 11/1996 | Potratz |
| 5,584,296 | A | 12/1996 | Cui et al. |
| 5,626,140 | A | 5/1997 | Feldman et al. |
| 5,803,910 | A | 9/1998 | Potratz |
| 5,934,277 | A | 8/1999 | Mortz |
| 6,385,471 | B1 | 5/2002 | Mortz |
| 6,438,399 | B1 | 8/2002 | Kurth |
| 6,453,183 | B1 | 9/2002 | Walker |
| 6,505,060 | B1 | 1/2003 | Norris |
| 6,510,329 | B2 | 1/2003 | Heckel |
| 6,599,251 | B2 | 7/2003 | Chen et al. |
| 6,668,182 | B2 | 12/2003 | Hubelbank |
| 6,714,803 | B1 | 3/2004 | Mortz |
| 6,754,516 | B2 | 6/2004 | Mannheimer |
| 6,896,661 | B2 | 5/2005 | Dekker |
| 6,987,994 | B1 | 1/2006 | Mortz |
| 7,001,337 | B2 | 2/2006 | Dekker |
| 7,221,969 | B2 | 5/2007 | Stoddart et al. |
| 7,268,873 | B2 | 9/2007 | Sevick-Muraca et al. |
| 7,744,541 | B2 | 6/2010 | Baruch et al. |
| 8,556,811 | B2 | 10/2013 | Brady |
| 2004/0097797 | A1 | 5/2004 | Porges et al. |
| 2005/0004479 | A1 | 1/2005 | Townsend et al. |
| 2005/0033129 | A1 | 2/2005 | Edgar, Jr. et al. |
| 2005/0192488 | A1 | 9/2005 | Bryenton et al. |
| 2005/0192493 | A1 | 9/2005 | Wuori |
| 2007/0004977 | A1 | 1/2007 | Norris |
| 2007/0049812 | A1 | 3/2007 | Aoyagi et al. |
| 2008/0081974 | A1 | 4/2008 | Pav |
| 2008/0146901 | A1 | 6/2008 | Katura et al. |
| 2008/0200785 | A1 | 8/2008 | Fortin |
| 2008/0228053 | A1 | 9/2008 | Wang et al. |
| 2009/0326386 | A1 | 12/2009 | Sethi et al. |
| 2010/0010322 | A1 | 1/2010 | Brady |
| 2010/0030054 | A1* | 2/2010 | Baruch .............. A61B 5/02007 600/368 |
| 2010/0049082 | A1 | 2/2010 | Hu et al. |
| 2011/0046459 | A1 | 2/2011 | Zhang et al. |
| 2011/0105912 | A1 | 5/2011 | Widman et al. |
| 2012/0149994 | A1 | 6/2012 | Luczyk et al. |
| 2012/0253211 | A1* | 10/2012 | Brady ................ A61B 5/02028 600/507 |
| 2012/0271130 | A1 | 10/2012 | Benni |
| 2013/0190632 | A1* | 7/2013 | Baruch ................ A61B 5/4064 600/484 |
| 2014/0073888 | A1* | 3/2014 | Sethi ....................... A61B 5/021 600/324 |
| 2014/0275818 | A1 | 9/2014 | Kassem et al. |
| 2014/0278285 | A1 | 9/2014 | Marmarelis et al. |
| 2016/0106372 | A1 | 4/2016 | Addison et al. |
| 2016/0324425 | A1 | 11/2016 | Addison et al. |
| 2016/0367197 | A1 | 12/2016 | Addison et al. |
| 2017/0000395 | A1 | 1/2017 | Addison et al. |
| 2017/0000423 | A1 | 1/2017 | Addison et al. |
| 2017/0095161 | A1 | 4/2017 | Addison et al. |
| 2017/0105631 | A1 | 4/2017 | Addison et al. |
| 2017/0105672 | A1 | 4/2017 | Addison et al. |

FOREIGN PATENT DOCUMENTS

| | | |
|---|---|---|
| WO | WO0059374 | 10/2000 |
| WO | WO03000125 A1 | 1/2003 |
| WO | WO03071928 A2 | 9/2003 |
| WO | WO2004075746 A2 | 9/2004 |
| WO | 2008097411 A1 | 8/2008 |
| WO | WO2008097411 A1 | 8/2008 |
| WO | WO2016182853 A1 | 11/2016 |

OTHER PUBLICATIONS

Addison, P. S.; "The Illustrated Wavelet Transform Handbook," 2002, IOP Publishing Ltd., Bristol, UK, Ch. 2.

Addison, Paul S., et al.; "A novel time-frequency-based 3D Lissajous figure method and its application to the determination of oxygen saturation from the photoplethysmogram," *Institute of Physic Publishing, Meas. Sci. Technol.*, vol. 15, pp. L15-L18 (2004).

Barreto, Armando B., et al.; "Adaptive LMS Delay Measurement in dual Blood Volume Pulse Signals for Non-Invasive Monitoring," *IEEE*, pp. 117-120 (1997).

Bassan, Haim, et al.; "Identification of pressure passive cerebral perfusion and its mediators after infant cardiac surgery," Pediatric Research Foundation, vol. 57, No. 1, 2005; pp. 35-41.

Belal, Suliman Yousef, et al.; "A fuzzy system for detecting distorted plethysmogram pulses in neonates and paediatric patients," *Physiol. Meas.*, vol. 22, pp. 397-412 (2001).

Brady, Ken M., et al.; "Continuous Measurement of Autoregulation by Spontaneous Fluctuations in Cerebral Perfusion Pressure Comparison of 3 Methods," NIH Public Access Author Manuscript, Stroke, 2008, 39(9), pp. 1-13.

Brady, Ken M., et al.; "Continuous time-domain analysis of cerebrovascular autoregulation using near-infrared spectroscopy," American Stroke Association, DOI:10.1161/strokeaha.107.485706, Aug. 2007, pp. 2818-2825.

Brady, Ken M., et al.; "Monitoring cerebral blood flow pressure autoregulation in pediatric patients during cardiac surgery," Stroke 2010;41:1957-1962 (http://stroke.ahajournals.org/content/41/9/1957.full).

Brady, Ken M., et al.; "Noninvasive Autoregulation Monitoring with and without Intracranial Pressure in a Naïve Piglet Brain," Neuroscience in Anesthesiology and Perioperative Medicine, 2010, Pressure vol. 111, No. 1, International Anesthesia Research Society, pp. 191-195.

Brady, Kenneth, et al.; "Real-Time Continuous Monitoring of Cerebral Blood Flow Autoregulation Using Near-Infrared Spectroscopy in Patients Undergoing Cardiopulmonary Bypass," Stroke, 2010, 41, American Heart Association, Inc., pp. 1951-1956.

Caicedo, Alexander, et al.; "Cerebral Tissue Oxygenation and Regional Oxygen Saturation Can be Used to study Cerebral Autoregulation in Prematurely Born Infants," Pediatric Research, vol. 69, No. 6, Jun. 1, 2011, pp. 548-553.

Caicedo, Alexander, et al.; "Detection of cerebral autoregulation by near-infrared spectroscopy in neonates: performance analysis of measurement methods," Journal of Biomedical Optics 17 (11) pp. 117003-1-117003-9 (Nov. 2012).

Chan, K.W., et al.; "17.3: Adaptive Reduction of Motion Artifact from Photoplethysmographic Recordings using a Variable Step-Size LMS Filter," IEEE, pp. 1343-1346 (2002)+A10.

Chen, Li, et al.; "The role of pulse oximetry plethysmographic waveform monitoring as a marker of restoration of spontaneous circulation: a pilot study," Chin Crit Care Med, 2015, vol. 27, No. 3, pp. 203-208.

Chen, Liangyou, et al.; "IS respiration-induced variation in the photoplethysmogram associated with major hypovolemia in patients with actue tramatic injuries," SHOCK, vol. 34, No. 5, pp. 455-460 (2010).

Cheng, Ran, et al.; "Noninvasive optical evaluation of spontaneous low frequency oscillations in cerebral hemodynamics", Neuroimage, Academic Press, vol. 62, No. 3, May 24, 2012, pp. 1445-1454.

Coetzee, Frans M.; "Noise-Resistant Pulse Oximetry Using a Synthetic Reference Signal," *IEEE Transactions on Biomedical Engineering*, vol. 47, No. 8, Aug. 2000, pp. 1018-1026.

Cyrill, D., et al.; "Adaptive Comb Filter for Quasi-Periodic Physiologic Signals," *Proceedings of the 25th Annual International Conference of the IEEE EMBS*, Cancun, Mexico, Sep. 17-21, 2003; pp. 2439-2442.

Cysewska-Sobusaik, Anna; "Metrological Problems With noninvasive Transillumination of Living Tissues," *Proceedings of SPIE*, vol. 4515, pp. 15-24 (2001).

Czosnyka, Marek, et al.; "Monitoring of cerebrovascular autoregulation: Facts, Myths, and Missing Links," Neurocrit Care (2009) 10:373-386.

(56) References Cited

OTHER PUBLICATIONS

Daubechies, Ingrid, et al.; "A Nonlinear Squeezing of the Continuous Wavelet Transform Based on Auditory Nerve Models," Princeton University, 1996, Acoustic Processing Department, NY, pp. iii, 1-17.

Daubechies, Ingrid, et al.; "Synchrosqueezed Wavelet Transforms: an Empirical Mode Decomposition-like Tool," Princeton University, 2010, Applied and Computational Harmonic Analysis, pp. 1-32.

Dias, Celeste, et al.; "Optimal Cerebral Perfusion Pressure Management at Bedside: A Single-Center Pilot Study," Neurocritical care, vol. 23, No. 1, Jan. 8, 2015; pp. 92-102; ISSN: 1541-6933.

East, Christine E., et al.; "Fetal Oxygen Saturation and Uterine Contractions During Labor," *American Journal of Perinatology*, vol. 15, No. 6, pp. 345-349 (Jun. 1998).

Edrich, Thomas, et al.; "Can the Blood Content of the Tissues be Determined Optically During Pulse Oximetry Without Knowledge of the Oxygen Saturation?—An In-Vitro Investigation," *Proceedings of the 20th Annual International conference of the IEEE Engie in Medicine and Biology Society*, vol. 20, No. 6, p. 3072-3075, 1998.

Eichhorn, Lars, et al.; "Evaluation of newar-infrared spectroscopy under apnea-dependent hypoxia in humans," Journal of Clinical Monitoring and Computing, vol. 29, No. 6, Feb. 4, 2015, pp. 749-757.

Gao, Yuanjuin, et al.; "Response of cerebral tissue oxygenation and arterial blood pressure to postural change assessed by wavelet phase coherence analysis", 2014 7th International conference on Biomedical Engineering and Informatics, IEEE, Oct. 14, 2014, pp. 373-377.

Ge, Z.; "Significance tests for the wavelet cross spectrum and wavelet linear coherence," Annales Geophysicae, 2008, 26, Copernicus Publications on behalf of European Geosciences Union, pp. 3819-3829.

Gesquiere, Michael J., et al., "Impact of withdrawal of 450 ML of blook on respiration-induced oscillations of the ear plethysmographic waveform," Journal of Clinical Monitoring and Computing (2007) 21:277-282.

Goldman, Julian M.; "Masimo Signal Extraction Pulse Oximetry," *Journal of Clinical Monitoring and Computing*, vol. 16, pp. 475-483 (2000).

Gommer, Erik D., et al.; "Dynamic cerebral autoregulation: different signal processing methods without influence on results and reproducibility"; Medical & Biological Engineering & Computer; vol. 48, No. 12, Nov. 4, 2010; pp. 1243-1250.

Hamilton, Patrick S., et al.; "Effect of Adaptive Motion-Artifact Reduction on QRS Detection," *Biomedical Instrumentation & Technology*, pp. 197-202 (May-Jun. 2000).

Huang, J., et al.; "Low Power Motion Tolerant Pulse Oximetry," Anesthesia & Analgesia 2002 94: S103.

Johansson, A.; "Neural network for photoplethysmographic respiratory rate monitoring," *Medical & Biological Engineering & Computing*, vol. 41, pp. 242-248 (2003).

Kaestle, S.; "Determining Artefact Sensitivity of New Pulse Oximeters in Laboratory Using Signals Obtained from Patient," *Biomedizinische Technik*, vol. 45 (2000).

Kim, J.M., et al.; "Signal Processing Using Fourier & Wavelet Transform for pulse oximetry," pp. II-310-II-311 (2001).

Kirkham, S.K., et al.; "A new mathematical model of dynamic cerebral autoregulation based on a flow dependent feedback mechanism; Dynamic cerebral autoregulation modelling," Physiological Measurement, Institute of Physics Publishing, vol. 22, No. 3, Aug. 1, 2001; (13 pgs.).

Leahy, Martin J., et al.; "Sensor Validation in Biomedical Applications," *IFAC Modelling and Control in Biomedical Systems*, Warwick, UK; pp. 221-226 (1997).

Lee, C.M., et al.; "Reduction of motion artifacts from photoplethysmographic recordings using wavelet denoising approach," *IEEE EMBS Asian-Pacific Conference on Biomedical Engineering*, Oct. 20-22, 2003; pp. 194-195.

Lee, Jennifer K., et al.; A pilot study of cerebrovascular reactivity autoregulation after pediatric cardiac arrest, Resuscitation 85, 2014, Elsevier Ireland Ltd., pp. 1387-1393.

Maletras, Francois-Xavier, et al.; "Construction and calibration of a new design of Fiber Optic Respiratory Plethysmograph (FORP)," *Optomechanical Design and Engineering, Proceedings of SPIE*, vol. 4444, pp. 285-293 (2001).

Massart, Desire L., et al.; "Least Median of Squares: A Robust Method for Outlier and Model Error Detection in Regression and Calibration," Analytica Chimica Acta, 1986, Elsevier Science Publishers B.V., The Netherlands, pp. 171-179.

McGrath, S.P., et al.; "Pulse oximeter plethysmographic waveform changes in awake, spontaneously breathing, hypovolemic volunteers," Anesth. Analg. vol. 112 No. 2, pp. 368-374 (2010).

Montgomery, Dean, et al.; "Data cluestering methods for the determination of cerebral autoregulation functionality," Journal of Clinical Monitoring and Computing, vol. 30, No. 5, Sep. 16, 2015, pp. 661-668.

Morren, G., et al.; "Detection of autoregulation in the brain of premature infants using a novel subspace-based technique," 23rd Annual International Conference of IEEE Engineering in Medicine and Biology Society, Oct. 2001; pp. 1-4.

Morren, Geert, et at; "Quantitation of the concordance between cerebral intravascular oxygenation and mean arterial blood pressure for the detection of impaired autoregulation," 29th Annual Meeting of the International Society on Oxygen Transport to Tissue, UofP, Aug. 2001; pp. 1-5.

Neumann, R., et al.; "Fourier Artifact suppression Technology Provides Reliable $SpO_2$," Anesthesia & Analgesia 2002, 94: S105.

Obrig, Hellmuth, et al.; "Spontaneous low frequency oscillations of cerebral heodynamics and metabolism in human adults," NeuroImage 12, 623-639 (2000).

Odagiri, Y.; "Pulse Wave Measuring Device," Micromechatronics, vol. 42, No. 3, pp. 6-11 (published Sep. 1998) (Article in Japanese—contains English summary of article).

Ono, Masahiro, et al.; "Validation of a stand-alone near-infrared spectroscopy system for monitoring cerebral autoregulaiton during cardiac surgery," International Anethesia Research Society, Jan. 2013, vol. 116, No. 1, pp. 198-204.

Panerai, B.; "Cerebral Autoregulation: from models to clinical Applications," Cardiovascular Engineering: an International Journal, vol. 8, No. 1, Nov. 28, 2007, (28 pgs.).

Payne, Stephen J., et al.; "Tissue Oxygenation Index as a Measure of Cerebral Autoregulation," Biomedial Engineering, Feb. 2004, Innsbruck, Austria, pp. 546-550.

Reinhard, Matthias, et al.; "Spatial mapping of dynamic cerebral autoregulation by multichannel near-infrared spectrosccopy in high-grade carotid artery disease", International Society for optical Engineering, SPIE, vol. 19, No. 9, Sep. 1, 2014, p. 97005.

Reinhard, Matthias, et al.; "Oscillatory cerebral hemodynamics—the macro- vs. microvascular level," Journal of the Neurological Sciences 250 (2006) 103-109.

Relente, A.R., et al.; "Characterization and Adaptive Filtering of Motion Artifacts in Pulse Oximetry using Accelerometers," *Proceedings of the Second joint EMBS/BMES Conference*, Houston, Texas, Oct. 23-26, 2002; pp. 1769-1770.

Rowley, A.B., et al.; "Synchronization between arterial blood pressure and cerebral oxyhaemoglobin concentration investigated by wavelet cross-correlation," Physiol. Meas., vol. 28, No. 2, Feb. 2007, pp. 161-173.

Shamir, M., et al.; "Pulse oximetry plethysmographic waveform during changes in blood volume," British Journal of Anaesthesia 82(2): 178-81 (1999).

Sorensen, Henrik, et al.; "A note on arterial to venous oxygen saturation as reference for NIRS-determined frontal lobe oxygen saturation in healthy humans," Frontiers in Physiology, vol. 4, Art. 403, Jan. 2014, pp. 1-3.

Stetson, Paul F.; "Determining Heart Rate from Noisey Pulse Oximeter Signals Using Fuzzy Logic," *The IEEE International Conference on Fuzzy Systems*, St. Louis, Missouri, May 25-28, 2003; pp. 1053-1058.

(56) References Cited

OTHER PUBLICATIONS

Such, Hans Olaf; "Optoelectronic Non-invasive Vascular Diagnostics Using multiple Wavelength and Imaging Approach," *Dissertation*, (1998).

Todd, Bryan, et al.; "The Identification of Peaks in Physiological Signals," *Computers and Biomedical Research*, vol. 32, pp. 322-335 (1999).

Tsuji, Miles, et al.; "Cerebral intravascular oxygenation correlates with mean arterial pressure in critically ill premature infants," American Academy of Pediatrics, 2000; 106; pp. 625-632.

Wagner, Bendicht P., et al.; "Dynanic cerebral autoregulatory response to blood pressure rise measured by near-infrared spectroscopy and intracranial pressure," Critical Care Medicine 2002, vol. 30, No. 9, pp. 2014-2021.

Whitaker, E., et al.; "Cerebrovascular Autoregulation After Pediatric Cardiac Arrest," NEURO—85, 2012, 2 pgs.

Williams, Monica, et al.; "Intraoperative blood pressure and Cerebral perfusion: strategies to clarify hemodynamic goals," Paediatric Anaesthesia, vol. 24, No. 7, Jul. 12, 2014; pp. 657-667; XP055331904.

Wong, Flora Y., et al.; "Impaired Autoregulation in preterm infants identified by using spatially resolved spectroscopy," American Academy of Pediatrics DOI:10.1542 (2008) e604-611.

Wu, Dongmei, et al.; "Na*/H* Exchange inhibition delays the onset of hypovolemic circulatory shock in pigs," Shock, vol. 29, No. 4, pp. 519-525 (2008).

Wu, et al.; "Using synchrosqueezing transform to discover breathing dynamics from ECG signals," arXiv:1105.1571, vol. 2, Dec. 2013, pp. 1-9.

Wu, Hau-tieng, et al.; "Evaluating physiological dynamics via Synchrosqueezing: Prediction of Ventilator Weaning," Journal of Latex Class Files, vol. 11, No. 4, Dec. 2012, pp. 1-9.

Zhang, Rong, et al.; "Transfer function analysis of dynamic cerebral autoregulation in humans," 1998 the American Physiological Society; pp. H233-241.

Zweifel, Christian, et al.; "Continuous time-domain monitoring of cerebral autoregulation in neurocritical care," Medical Engineering & Physics, Elsevier Ltd., vol. 36, No. 5, 2014, pp. 638-645.

U.S. Appl. No. 15/648,665, filed Jul. 13, 2017, Dean Montgomery.

U.S. Appl. No. 15/666,167, filed Aug. 1, 2017, naming inventors Addison et al.

Chuan et al., "Is cerebrovascular autoregulation associated with outcomes after major noncardiac surgery? A prospective observational pilot study," Acta Anaesthesiol Scand., Aug. 5, 2018, 10 pp.

\* cited by examiner

SYSTEMS AND METHODS FOR OPTIMIZING AUTOREGULATION MEASUREMENTS

CROSS REFERENCE TO RELATED APPLICATION

This application claims priority from and the benefit of U.S. Provisional Patent Application No. 62/166,973, filed May 27, 2015, entitled "Systems and Methods for Optimizing Autoregulation Measurements," which is incorporated by reference herein in its entirety.

BACKGROUND

The present disclosure relates generally to medical devices and, more particularly, to systems and methods for monitoring autoregulation of a patient.

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

In the field of medicine, medical professionals often desire to monitor certain physiological parameters of their patients. In some cases, clinicians may wish to monitor a patient's autoregulation. Autoregulation is a physiological process that attempts to maintain an optimal cerebral blood flow to supply appropriate levels of oxygen and nutrients to the brain. During autoregulation, cerebral arterioles dilate or constrict to maintain optimal blood flow. For example, as cerebral pressure decreases, cerebral arterioles dilate in an attempt to maintain blood flow. As cerebral pressure increases, cerebral arterioles constrict to reduce the blood flow that could cause injury to the brain. If the patient's autoregulation process is not functioning properly, the patient may experience inappropriate cerebral blood flow, which may have negative effects on the patient's health. In particular, a drop in cerebral blood flow may cause ischemia, which may result in tissue damage or death of brain cells. An increase in cerebral blood flow may cause hyperminia, which may result in swelling of the brain or edema.

Some existing systems for monitoring autoregulation may determine a patient's autoregulation status based on various physiological signals. For example, some existing systems may determine if the patient's autoregulation process is intact (e.g., functioning properly), impaired (e.g., not functioning properly), and/or transitioning from intact to impaired. Such physiological values may be subject to various sources of error, such as noise caused by emotions, operator error, poor quality measurements, drugs, or other anomalies. However, existing systems for monitoring autoregulation may not reduce the various sources of error when utilizing the measured physiological values to determine the patient's autoregulation status. Accordingly, existing systems may not accurately determine if a patient's autoregulation status is functioning properly or may not determine if the patient's autoregulation is approaching impaired function.

BRIEF DESCRIPTION OF THE DRAWINGS

Advantages of the disclosed techniques may become apparent upon reading the following detailed description and upon reference to the drawings in which.

DETAILED DESCRIPTION OF SPECIFIC EMBODIMENTS

One or more specific embodiments of the present techniques will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

A physician may monitor a patient's autoregulation through the use of various monitoring devices and systems. In accordance with the present disclosure, a patient's autoregulation may be monitored by correlating measurements of the patient's blood pressure (e.g., arterial blood pressure) with measurements of the patient's oxygen saturation (e.g., regional oxygen saturation). In particular, a regional oxygen saturation ($rSO_2$) curve may be derived based at least in part on one or more linear correlations (or one or more pairs of linear correlations) between the patient's blood pressure and oxygen saturation. In certain embodiments of the present disclosure, the system for monitoring autoregulation may determine a patient's autoregulation status based on the $rSO_2$ curve and/or based on one or more values derived from the $rSO_2$ curve. For example, in certain situations, it may be beneficial to determine an upper limit of autoregulation (ULA) value and/or a lower limit of autoregulation (LLA) value from the $rSO_2$ curve. Indeed, the ULA and LLA approximately define an upper and a lower boundary within which autoregulation is generally intact and functioning properly. Likewise, regions of the rSO$_2$ curve approximately above the ULA and/or approximately below the LLA may be indicative of impaired autoregulation function.

The disclosed systems and methods may accurately determine the LLA value, which may then be used to reliably evaluate the patient's autoregulation. While features of this disclosure are described with respect to determining the LLA value, it should be noted that in certain embodiments, the disclosed systems and methods may be utilized to accurately determine the ULA value or any other point of interest or value on the rSO$_2$ curve. As noted above, the LLA value may be defined as approximately the point on the rSO$_2$ curve where the autoregulation of the patient transitions from impaired to intact. However, during patient monitoring, physiological values used to determine the rSO$_2$ curve may be affected by noise. Accordingly, the disclosed methods may enable the system to ignore or exclude data outliers indicative of noise, and to utilize the remaining data to accurately determine the rSO$_2$ curve and the LLA value on the rSO$_2$ curve. Further, the disclosed methods may enable the system to optimize the determination of the LLA point on the rSO$_2$ curve.

In certain embodiments, such as in ideal situations where measurements obtained from the patient do not include data outliers indicative of noise, the system may determine the rSO$_2$ curve based on two regression lines (e.g., best fit lines), and determine the LLA value by identifying the point on the rSO$_2$ curve where the slope changes between the two regression lines. In certain embodiments, such as in non-ideal situations where measurements obtained from the patient include data outliers indicative of noise, the system may be configured to algorithmically determine a plurality of regression lines and identify the most suitable pair of regression lines. Specifically, the system may bin the patient's oxygen saturation measurements based on the patient's blood pressure measurements according to one or more pre-determined variables and/or rules. Further, based on the generated bins, the system may generate a plurality of regression lines and may identify the most suitable pair of regression lines based on one or more rules, as further discussed in detail below. As noted above, the system may determine the LLA value by identifying the point on the rSO$_2$ curve where the slope changes from positive to negative between the most suitable pair of regression lines. Accordingly, the system may be configured to optimize the determination of the LLA point on the rSO$_2$ curve to efficiently and accurately monitor a patient's autoregulation status, as further described with respect to FIGS. 2A-8.

While features of the present disclosure are discussed with reference to rSO$_2$ and the rSO$_2$ curve, it should be noted that in other embodiments, various other signals may be determined to help evaluate a patient's autoregulation. For example, the relationship between a patient's blood pressure measurements and NIRS derived blood volume measurements (BVS) may be used to derive a BP-BVS curve. Likewise, the relationship a patient's blood pressure and measurements of a patient's cerebral blood flow may derive a BP-Flow curve. As a further example, the relationship between measurements of a patient's blood pressure and measurements of a patient's intracranial pressure (ICP) may derive a BP-ICP curve. In certain situations, the systems and methods described herein may be utilized to determine values on the curves (e.g., upper and/or lower limits) that may be helpful in evaluating a patient's autoregulation.

Figures 1, 2A:
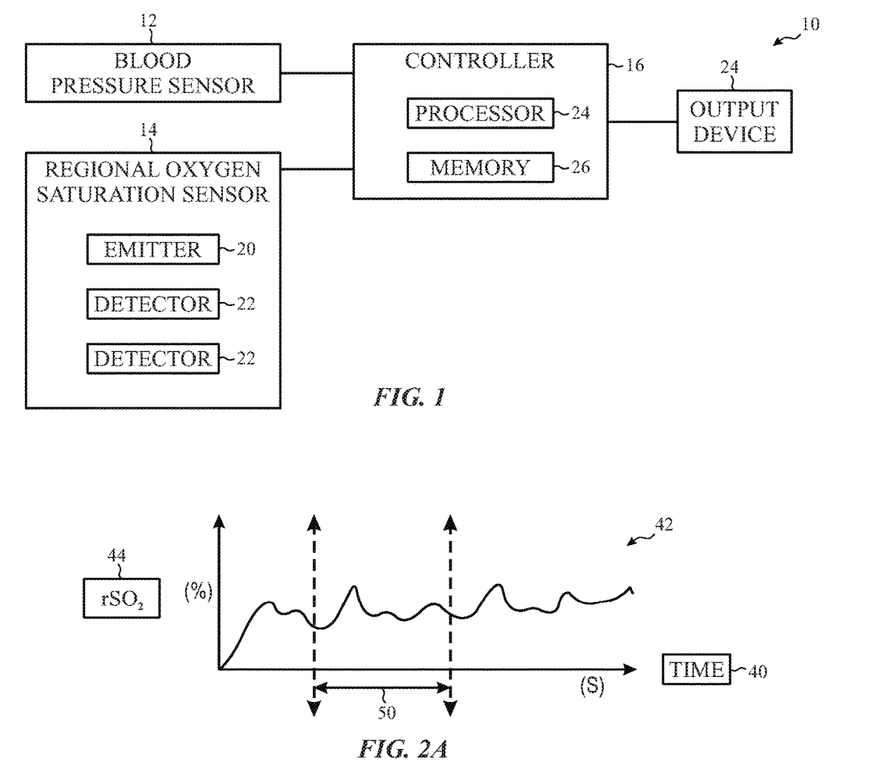
FIG. 1 is a block diagram of an embodiment of a system for monitoring an autoregulation of a patient.
FIG. 2A is an example of a graph illustrating a regional oxygen saturation value obtained from the patient over a period of time.

FIG. 1 illustrates an embodiment of a system 10 for monitoring autoregulation. As shown, the system 10 includes a blood pressure sensor 12, an oxygen saturation sensor 14 (e.g., a regional oxygen saturation sensor 14), a controller 16, and an output device 18. The blood pressure sensor 12 may be any sensor or device configured to obtain the patient's blood pressure (e.g., arterial blood pressure). For example, the blood pressure sensor 12 may include a blood pressure cuff for non-invasively monitoring blood pressure or an arterial line for invasively monitoring blood pressure. In certain embodiments, the blood pressure sensor 12 may include one or more pulse oximetry sensors. In some such cases, the patient's blood pressure may be derived by processing time delays between two or more characteristic points within a single plethysmography (PPG) signal obtained from a single pulse oximetry sensor. Various techniques for deriving blood pressure based on a comparison of time delays between certain components of a single PPG signal obtained from a single pulse oximetry sensor is described in U.S. Publication No. 2009/0326386, entitled "Systems and Methods for Non-Invasive Blood Pressure Monitoring," the entirety of which is incorporated herein by reference. In other cases, the patient's blood pressure may be continuously, non-invasively monitored via multiple pulse oximetry sensors placed at multiple locations on the patient's body. As described in U.S. Pat. No. 6,599,251, entitled "Continuous Non-invasive Blood Pressure Monitoring Method and Apparatus," the entirety of which is incorporated herein by reference, multiple PPG signals may be obtained from the multiple pulse oximetry sensors, and the PPG signals may be compared against one another to estimate the patient's blood pressure. Regardless of its form, the blood pressure sensor 12 may be configured to generate a blood pressure signal indicative of the patient's blood pressure (e.g., arterial blood pressure) over time. As discussed in more detail below, the blood pressure sensor 12 may provide the blood pressure signal to the controller 16 or to any other suitable processing device to enable evaluation of the patient's autoregulation status.

As shown, the oxygen saturation sensor 14 may be a regional oxygen saturation sensor configured to generate an oxygen saturation signal indicative of blood oxygen saturation within the venous, arterial, and capillary systems within a region of the patient. For example, the oxygen saturation sensor 14 may be configured to be placed on the patient's forehead and may be used to calculate the oxygen saturation of the patient's blood within the venous, arterial, and capillary systems of a region underlying the patient's forehead (e.g., in the cerebral cortex).

In such cases, the oxygen saturation sensor 14 may include an emitter 20 and multiple detectors 22. The emitter 20 may include at least two light emitting diodes (LEDs), each configured to emit at different wavelengths of light, e.g., red or near infrared light. In one embodiment, the LEDs of the emitter 20 emit light in the range of about 600 nm to about 1000 nm. In a particular embodiment, one LED of the emitter 20 is configured to emit light at about 730 nm and the other LED of the emitter 20 is configured to emit light at about 810 nm. One of the detectors 22 is positioned relatively "close" (e.g., proximal) to the emitter 20 and one of the detectors 22 is positioned relatively "far" (e.g., distal) from the emitter 22. Light intensity of multiple wavelengths may be received at both the "close" and the "far" detectors 22. For example, if two wavelengths are used, the two wavelengths may be contrasted at each location and the resulting signals may be contrasted to arrive at a regional saturation value that pertains to additional tissue through which the light received at the "far" detector passed (tissue in addition to the tissue through which the light received by the "close" detector passed, e.g., the brain tissue), when it was transmitted through a region of a patient (e.g., a patient's cranium). Surface data from the skin and skull may be subtracted out, to generate a regional oxygen saturation ($rSO_2$) signal for the target tissues over time. As discussed in more detail below, the oxygen saturation sensor 14 may provide the regional oxygen saturation signal to the controller 16 or to any other suitable processing device to enable evaluation of the patient's autoregulation status.

In operation, the blood pressure sensor 12 and the oxygen saturation sensor 14 may each be placed on the same or different parts of the patient's body. Indeed, the blood pressure sensor 12 and the oxygen saturation sensor 14 may in some cases be part of the same sensor or supported by a single sensor housing. For example, the blood pressure sensor 12 and the oxygen saturation sensor 14 may be part of an integrated oximetry system configured to non-invasively measure blood pressure (e.g., based on time delays in a PPG signal) and regional oxygen saturation. One or both of the blood pressure sensor 12 or the oxygen saturation sensor 14 may be further configured to measure other parameters, such as hemoglobin, respiratory rate, respiratory effort, heart rate, saturation pattern detection, response to stimulus such as bispectral index (BIS) or electromyography (EMG) response to electrical stimulus, or the like. While an exemplary system 10 is shown, the exemplary components illustrated in FIG. 1 are not intended to be limiting. Indeed, additional or alternative components and/or implementations may be used.

As noted above, the blood pressure sensor 12 may be configured to provide the blood pressure signal to the controller 16, and the oxygen saturation sensor 14 may be configured to provide the oxygen saturation signal to the controller 16. In certain embodiments, the controller 16 is an electronic controller having electrical circuitry configured to process the various received signals. In particular, the controller 16 may be configured to process the blood pressure signal and the oxygen saturation signal to evaluate the patient's cerebral autoregulation status. Although the blood pressure sensor 12 and the oxygen saturation sensor 14 may be configured to provide their respective signals or data directly to the controller 16, in certain embodiments, the signals or data obtained by the blood pressure sensor 12 and/or the oxygen saturation sensor 14 may be provided to one or more intermediate processing devices (e.g., specialized monitor, such as a blood pressure monitor or an oxygen saturation monitor, or the like), which may in turn provide processed signals or data to the controller 16.

As discussed in more detail below, the controller 16 may be configured to determine a regional oxygen saturation ($rSO_2$) curve based on the blood pressure signal and the oxygen saturation signal. In certain embodiments, the $rSO_2$ curve may be indicative of whether the patient's autoregulation is intact or impaired. The controller 16 may derive the $rSO_2$ curve by determining linear correlations between blood pressure measurements and oxygen saturation measurements. For example, when a pair of regression lines are fit to determine the $rSO_2$ curve, the point or value on the curve where the slope transitions from a positive slope to a flat or negative slope may suggest that the cerebral autoregulation is transitioning from impaired to intact, and may be associated with the lower limit of autoregulation (LLA) value. Accordingly, a regression line with a relatively flat or negative slope may suggest that cerebral autoregulation is working properly, while a regression line with a positive may suggest that the cerebral autoregulation is impaired.

In certain embodiments, it may be beneficial to determine the LLA value (and/or an upper limit of autoregulation value (ULA)) on the $rSO_2$ curve (e.g., one or more regression lines) in order to monitor the autoregulation of the patient and determine approximately when the autoregulation transitions from intact to impaired. As noted above, the autoregulation of the patient fails to function properly (e.g., impaired) when the cerebral pressure is too high and blood flow is insufficient or when the cerebral pressure is too low and blood flow is excessive. In some ideal situations, the LLA value on the $rSO_2$ curve may be easily determined based on a change in the slope (e.g., from positive slope to negative slope) of a pair of regression lines that make up the $rSO_2$ curve. In non-ideal situations, such as in situations where signal noise is a factor, the controller 16 may be configured to determine a plurality of regression lines and identify the most suitable pair of regression lines. The controller 16 may utilize the identified pair of regression lines to determine the LLA value. Specifically, the controller 16 may determine the most suitable pair of regression lines by generating bins based on the measurements, generating one or more regression lines based on the bins, and identifying the pair of regression lines that exclude or ignore outliers indicative of noise, as further described with respect to FIGS. 5-7.

In certain embodiments, the controller 16 may be configured to determine a significance value (e.g., a p-value) associated with the linear correlations of the blood pressure measurements and the oxygen saturation measurements. The p-value may indicate whether certain $rSO_2$ values, or portions of $rSO_2$ curve generated based on such values, are reliable or unreliable. For example, the p-value may enable the controller 16 to identify portions of the $rSO_2$ curve that are adversely affected by noise, and which are therefore unreliable. As discussed in detail with respect to FIG. 7, in certain embodiments, the controller 16 may use the p-value to determine the most suitable pair of regression lines.

In the illustrated embodiment, the controller 16 includes a processor 24 and a memory device 26. The controller 16 may also include one or more storage devices. The processor 24 may be used to execute software, such as software for carrying out any of the techniques disclosed herein, such as processing the blood pressure signals and/or oxygen saturation signals, determining the $rSO_2$ curve, determining one or more regression lines, determining or identifying the most appropriate pair of regression lines, determining an LLA value (or ULA value), calculating a significance value (p-value), carrying out appropriate remedial actions, and so forth. Moreover, the processor 24 may include multiple microprocessors, one or more "general-purpose" microprocessors, one or more special-purpose microprocessors, and/or one or more application specific integrated circuits (ASICS), or some combination thereof. For example, the processor 24 may include one or more reduced instruction set (RISC) processors.

The memory device 26 may include a volatile memory, such as random access memory (RAM), and/or a nonvolatile memory, such as ROM. The memory device 26 may include one or more tangible, non-transitory, machine-readable media collectively storing instructions executable by the processor 24 to perform the methods and control actions described herein. Such machine-readable media can be any available media that can be accessed by the processor 24 or by any general purpose or special purpose computer or other machine with a processor. The memory device 26 may store a variety of information and may be used for various purposes. For example, the memory device 26 may store processor-executable instructions (e.g., firmware or software) for the processor 24 to execute, such as instructions for carrying out any of the techniques discloses herein, such as processing the blood pressure signal and/or the oxygen saturation signal, determining the $rSO_2$ curve, determining one or more regression lines, determining or identifying the most appropriate pair of regression lines, determining an LLA value (or ULA value), calculating a significance value (p-value), carrying out appropriate remedial actions, and so forth. The storage device(s) (e.g., nonvolatile storage) may include read-only memory (ROM), flash memory, a hard drive, or any other suitable optical, magnetic, or solid-state storage medium, or a combination thereof. The storage device(s) may store data (e.g., the blood pressure signal, the oxygen saturation signal, the $rSO_2$ curve, the one or more regression lines, the LLA value (or ULA value), the p-value, etc.), instructions (e.g., software or firmware for processing the blood pressure signal and/or the oxygen saturation signal, determining the $rSO_2$ and/or the p-value, and/or taking appropriate remedial actions), predetermined thresholds, and any other suitable data.

As shown, the system 10 includes the output device 18. In some embodiments, the controller 16 may be configured to provide signals indicative of the patient's autoregulation status to the output device 18. As discussed in more detail below, the controller 16 may be configured to generate an alarm signal indicative of the patient's autoregulation status and to provide the alarm signal to the output device 18. The output device 18 may include any device configured to receive signals (e.g., the signal indicative of the patient's autoregulation status, the alarm signal, or the like) from the controller 16 and visually and/or audibly output information indicative of the patient's autoregulation status (e.g., the $rSO_2$ curve or value, the LLA value (or ULA value), an alarm, or the like). For instance, the output device 18 may include a display configured to provide a visual representation of the patient's autoregulation status and/or the alarm signal as determined by the controller 16. Additionally or alternatively, the output device 18 may include an audio device (e.g., speaker) configured to provide sounds in accordance with the alarm signal, the patient's autoregulation status, or both. The output device 18 may be any suitable device for conveying such information, including a computer workstation, a server, a desktop, a notebook, a laptop, a handheld computer, a mobile device, or the like. In some embodiments, the controller 16 and the output device 18 may be part of the same device or supported within one housing (e.g., a computer or monitor).

Figure 2B:
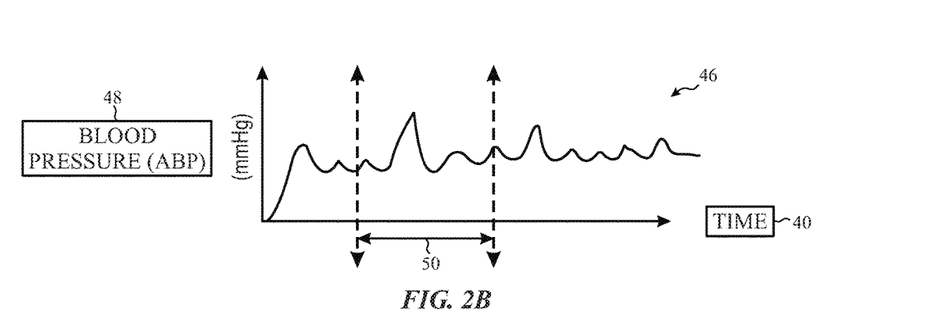
FIG. 2B is an example of a graph illustrating a blood pressure value obtained from the patient over a period of time.

FIGS. 2A-2B are examples of graphs illustrating physiological values obtained from a patient over a period of time 40 from one or more sensors. Specifically, FIG. 2A is an example of a graph 42 illustrating an oxygen saturation value 44 (e.g., regional oxygen saturation value, $rSO_2$, etc.) obtained from the patient over the period of time 40 from the regional oxygen saturation sensor 14. In addition, FIG. 2B is an example of a graph 46 illustrating a blood pressure value 48 obtained over the period of time 42 from the blood pressure sensor 12. As noted above, in certain embodiments, other types of physiological signals may be measured and provided to the controller 16, such as any physiological signal that may be useful in determining an autoregulation status of a patient (e.g., blood volume, intracranial pressure, blood flow, cerebral blood flow, etc.).

The period of time 40 over which the physiological values (e.g., the regional oxygen saturation values 44 and/or the blood pressure values 48) are measured may be different for each signal and/or each sensor, and may be provided to the controller 16 continuously or intermittently over the period of time 40. In certain embodiments, a history of the physiological values may be gathered over the period of time 40 over several minutes (e.g., approximately 5-10 minutes, 10-30 minutes, 30-60 minutes, or more) or hours (e.g., approximately 1-2 hours, 2-5 hours, 5-10 hours, or more). Further, the physiological values may be gathered in different locations within a hospital setting or during different procedures.

The controller 16 may be configured to monitor autoregulation of a patient based on one or more of the physiological signals received from the patient. Specifically, the controller 16 may determine the $rSO_2$ curve based in part on a linear correlation between the oxygen saturation signal 46 and the blood pressure signal 48, and utilize the $rSO_2$ curve to determine an indication of the patient's autoregulation. In particular, the controller 16 may plot the oxygen saturation measurements derived from the oxygen saturation values 44 against blood pressure measurements derived from the blood pressure values 48 over an overlapping analysis window 50 having a particular length of time. The analysis window 50 may be any portion of the period of time 42 where two physiological signals are measured from the same patient at the same time. As described in detail with respect to FIGS. 3-4, the controller 16 may plot the oxygen saturation measurements against the blood pressure measurements over the analysis window 50 to determine linear correlations (e.g., regression lines) between measurements obtained at the same time. The analysis window 50 may include a series of time points, and each plotting the oxygen saturation measurements against the blood pressure measurements may include associating each oxygen saturation measurement with a corresponding blood pressure measurement according to a time point.

Figure 3:
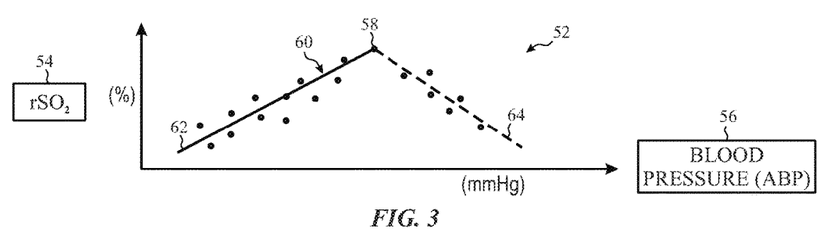
FIG. 3 is an example of a graph illustrating a pair of linear correlations between the oxygen saturation measurements and the blood pressure measurements to determine a LLA value.

FIG. 3 is an example of a first graph 52 illustrating a pair of linear correlations between oxygen saturation measurements 54 and the blood pressure measurements 56 to determine a LLA value 58. As noted above, the oxygen saturation measurements 54 and the blood pressure measurements 56 may be derived from the oxygen saturation values 44 and the blood pressure values 48, respectively. Additionally, as noted above, these physiological measurements may be plotted against each other over the analysis window 50. In particular, the controller 16 may derive an $rSO_2$ curve 60 by determining a pair of linear correlations between the blood pressure measurements 56 and the oxygen saturation measurements 54. The result of the pair of linear correlations may be one or more regression lines (e.g., best fit lines) between oxygen saturation measurements and blood pressure measurements, and the slope of the regression lines may be indicative of the patient's autoregulation status.

In the illustrated embodiment, the controller 16 may determine a pair of regression lines based on linear correlation between the oxygen saturation measurements 54 and the blood pressure measurements 56. In certain embodiments, the controller 16 may determine the regression lines by minimizing the total residual squared error (RSE) of the measurements. Accordingly, a left regression line 62 may be associated with a linear correlation between the oxygen saturation measurements 54 and the blood pressure measurements 56 on the left side of the LLA value 58. Likewise, a right regression line 64 may be associated with a linear correlation between the oxygen saturation measurements 54 and the blood pressure measurements 56 on the right side of the LLA value 58. As noted above, the LLA value 58 may be indicative of the autoregulation of the patient transitioning from impaired to intact. For example, in the illustrated embodiment, the slope of the left regression line 62 is positive (e.g., impaired autoregulation) and the slope of the right regression line 64 is negative (e.g., intact autoregulation). In particular, the LLA value 58 is approximately the point where the autoregulation transitions from impaired to intact. Accordingly, it may be beneficial to accurately determine the LLA value to effectively monitor a patient's autoregulation status or condition.

In certain ideal situations, the physiological measurements derived from the patient may include little to no signal noise. For example, in the illustrated embodiment, the oxygen saturation measurements 54 and the blood pressure measurements 56 do not include any clear data outliers indicative of signal noise that bias the regression lines. Accordingly, the controller 16 may be configured to accurately determine the left regression line 62 and the right regression line 64 that make up the $rSO_2$ curve 60. Further, the controller 16 may be configured to accurately determine the LLA value 58 based on the pair of regression lines. Indeed, in ideal situations, the controller 16 may determine a reliable LLA value 58 without additional computation or analysis. However, in typical patient monitoring situations, the physiological measurements or signals obtained from the patient are subject to various sources of error that cause data outliers. For example, as further discussed with respect to FIG. 4, in non-ideal situations, the controller 16 may not be able to reliably determine the LLA value 58. Accordingly, as further described with respect to FIGS. 5-8, for non-ideal situations, the controller 16 may be configured to algorithmically determine a plurality of regression lines and identify the most suitable pair of regression lines.

Figure 4:
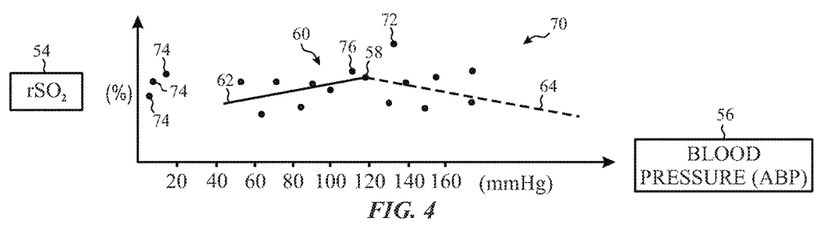
FIG. 4 is an example of a graph illustrating a pair of linear correlations between the oxygen saturation measurements and the blood pressure measurements that excludes data measurements indicative of noise.

FIG. 4 is an example of a second graph 70 illustrating a pair of linear correlations between oxygen saturation measurements 54 and the blood pressure measurements 56 to determine the LLA value 58. Specifically, the illustrated embodiment depicts one or more outliers 72, 74 indicative of signal noise that may bias the left regression line 62 and/or the right regression line 64. Accordingly, the LLA value 58 determined from the left and right regression lines 62 and 64, respectively, may not be a reliable indication of the autoregulation status of the patient. For example, one or more other values 76 disposed on the $rSO_2$ curve 60 may be a more accurate and/or a more reliable indication of the autoregulation status of the patient.

In certain embodiments, the controller 16 may be configured to exclude or ignore one or more outliers 72, 74 and utilize the remaining data to determine the linear correlations (e.g., regression lines). For example, in certain situations, the controller 16 may ignore or exclude blood pressure measurements 56 less than a predetermined threshold value in order to remove measurements that are most likely outliers. In the illustrated embodiment, the controller 16 may exclude or ignore the outliers 74 having a blood pressure measurement less than approximately 20 mmHg. It should be noted that in other embodiments, the pre-determined threshold may be any blood pressure value, such as approximately less than 60 mmHg, 50 mmHg, 40 mmHg, 30 mmHg, 15 mmHg, 10 mmHg, 5 mmHg, or less. Further, in certain embodiments, the pre-determined threshold may be any oxygen saturation value, such as any oxygen saturation value approximately less than 50%, 40%, 30%, 20%, 15%, 10%, 5%, or less.

However, in certain situations, removing one or more portions of the outliers 74 may not remove all of the outliers 72, 74, and the resulting regression lines may be susceptible to the remaining outliers 72. Accordingly, as further described with respect to FIGS. 5-8, the controller 16 may be configured to algorithmically determine a plurality of regression lines and identify the most suitable pair of regression lines in order to determine the LLA value 58. In particular, the most suitable pair of regression lines may minimize the effect of the outliers to determine a pair of regression lines that may be used to reliably calculate the LLA value 58.

Figure 5:
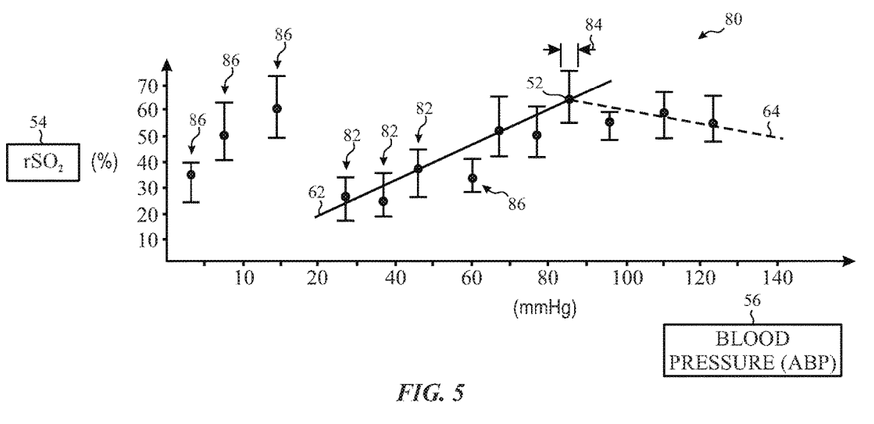
FIG. 5 is an example of a graph illustrating a pair of linear correlations between the oxygen saturation measurements and the blood pressure measurements generated by binning the measurements.

FIG. 5 is an example of a graph 80 illustrating a pair of linear correlations between the oxygen saturation measurements 54 and the blood pressure measurements 56, where the pair of linear correlations is generated from the binned $rSO_2$. Specifically, the controller 16 may generate a plurality of bins 82 for the oxygen saturation measurements 54 based on the blood pressure measurements 56 at each corresponding time point from the analysis window 50. In addition, the controller 16 may calculate a median or mean of each bin 82 to determine one or more regression lines that best fit the data. In particular, the controller 16 may bin measurements in this manner so that the generated regression lines are not as sensitive to outliers 72, 74, thereby allowing the controller 16 to generate regression lines that are more accurate and less susceptible to signal noise, as further described below.

In certain embodiments, the controller 16 may bin the oxygen saturation measurements 54 based on the blood pressure measurements 56 (or vise versa) to reduce the effects of minor observations and/or measurements. For example, the controller 16 may generate a bin 82 for each time point having a width 84 of 5 mmHg units. In particular, binning measurements may be associated with grouping certain measurements such that each bin 82 may include or represent a certain number of original data measurements. For example, each bin 82 may be representative of a number of original measurements that fall within a particular interval or width 84. Indeed, a number or quantity of original measurements (e.g., samples) may be replaced by the bin 82 configured to represent those samples. It should be noted that the width 84 or interval of the bin may be a pre-defined value stored within the memory device 26, and may be any value greater than 0 mmHg units, between approximately 0 and 3 mmHg units, between approximately 3 and 5 mmHg units, or greater than 5 mmHg units. In certain embodiments, the width 84 of each bin 82 may be determined based on a quality or an amount of data received from the sensors. In addition, each bin 82 may include or represent any number of original measurements or samples. For example, in certain situations, the bin 82 may replace 1-5 samples, 5-10 samples, 10-20 samples, 20-50 samples, or more than 50 samples. In certain embodiments, the number of samples that each bin 82 replaces or represents may be dependent on the quality of samples obtained, a sampling rate of the sensors, a signal quality metric, and/or any combination thereof. In addition, the controller 16 may calculate a median or mean of each bin 82 to determine one or more regression lines that best fit the data.

As noted above, in certain situations, the controller 16 may exclude or ignore data outliers 74 (e.g., measurements indicative of signal noise) that are less a pre-determined threshold when calculating the one or more regression lines. For example, in the illustrated embodiment, blood pressure measurements less than approximately 20 mmHg may be excluded from the regression line generated by the controller 16. It should be noted that in other embodiments, the pre-determined threshold may be any blood pressure value, such as approximately less than 60 mmHg, 50 mmHg, 40 mmHg, 30 mmHg, 15 mmHg, 10 mmHg, 5 mmHg, or less.

Further, in certain embodiments, the pre-determined threshold may be any oxygen saturation value, such as any oxygen saturation value approximately less than 50%, 40%, 30%, 20%, 15%, 10%, 5%, or less. In addition, in certain embodiments, the controller 16 may utilize the remaining data to calculate the bins 82 and calculate a mean/median of the bins to determine one or more regression lines.

As a further example, in certain situations, the controller 16 may exclude or ignore one or more bins 86 that represent or include original measurements that are likely outliers 72, 74 when calculating the mean/median of the bins 82. For example, the controller 16 may exclude or ignore bins 86 that include measurements less than a predefined threshold, as noted above. Further, the controller 16 may exclude or ignore bins 86 that include less than a predefined number of samples. For example, in certain embodiments, the controller 16 may exclude or ignore bins 86 that have less than 5 samples of original data. It should be noted that the minimum threshold for the number of samples may be less than 10 samples, less than 8 samples, less than 4 samples, or less than 3 samples. Based on the remaining measurements and/or bins 82, the controller 16 may be configured to calculate the median or mean of the bins 82. Further, the controller 16 may determine one or more regression lines (e.g., left side regression line 62 and/or right side regression line 64) based on the calculated mean or median of the bins 82. In certain embodiments, a plurality of regression lines, such as a plurality of left side regression lines 62 and/or a plurality of right side regression lines 64 may be determined based on the mean or median of the bins 82, as further described with respect to FIG. 6. The controller 16 may determine the best or most suitable pair of regression lines (e.g., a left side regression line and a right side regression line) in order to calculate, for example, the LLA value, as further described with respect to FIG. 7.

Figure 6:
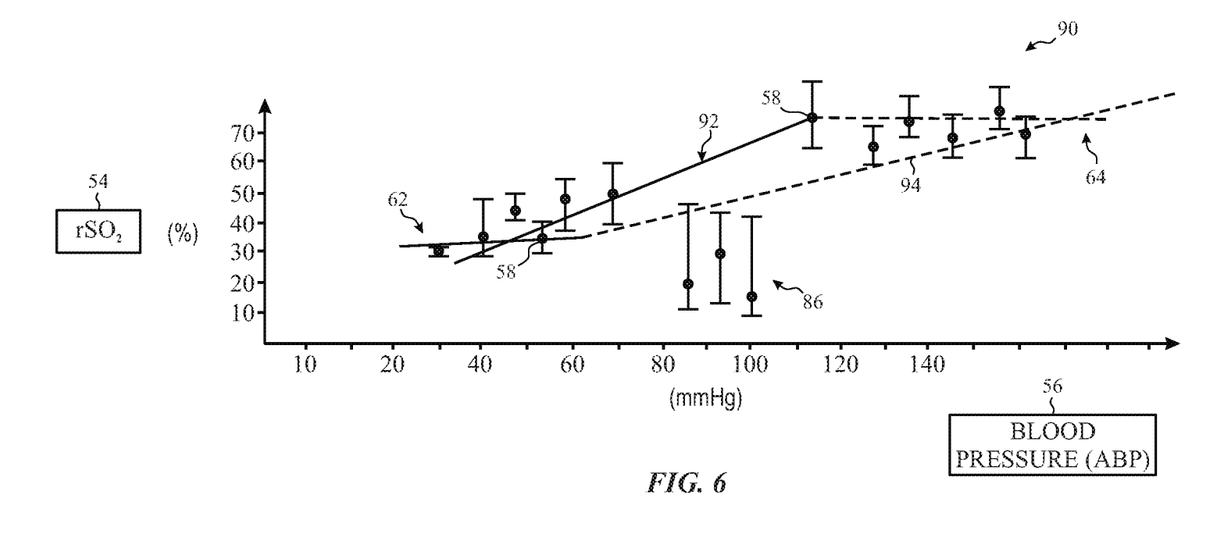
FIG. 6 is an example of a graph illustrating a plurality of pairs of linear correlations between the oxygen saturation measurements and the blood pressure measurements generated by binning the measurements.

FIG. 6 is an example of a graph 90 illustrating a plurality of linear correlations between the oxygen saturation measurements 54 and the blood pressure measurements 56. As noted above, based on the mean or median of the bins 82, the controller 16 may generate a plurality of regression lines. Specifically, the controller 16 may generate one or more left side regression lines 62 and one or more right side regression lines 64. In certain embodiments, the controller 16 may be configured to determine the most suitable pair of regression lines (e.g., left side regression line and right side regression line) based on one or more analyses, as further described with respect to FIG. 7. In certain embodiments, the controller 16 may be configured to calculate the plurality of regression lines before one or more bins 86 are excluded and after one or more bins 86 are excluded. For example, in the illustrated embodiment, a first pair of regression lines 92 may be calculated after excluding or ignoring one or more bins 86 with particularly low blood pressure measurements 56 and a second pair of regression lines 94 may be calculated before excluding or ignoring the one or more bins 86. The controller 16 may be configured to determine the most suitable pair of regression lines 92, 94 based on one or more analyses or techniques, as further described with respect to FIG. 7.

Figure 7:
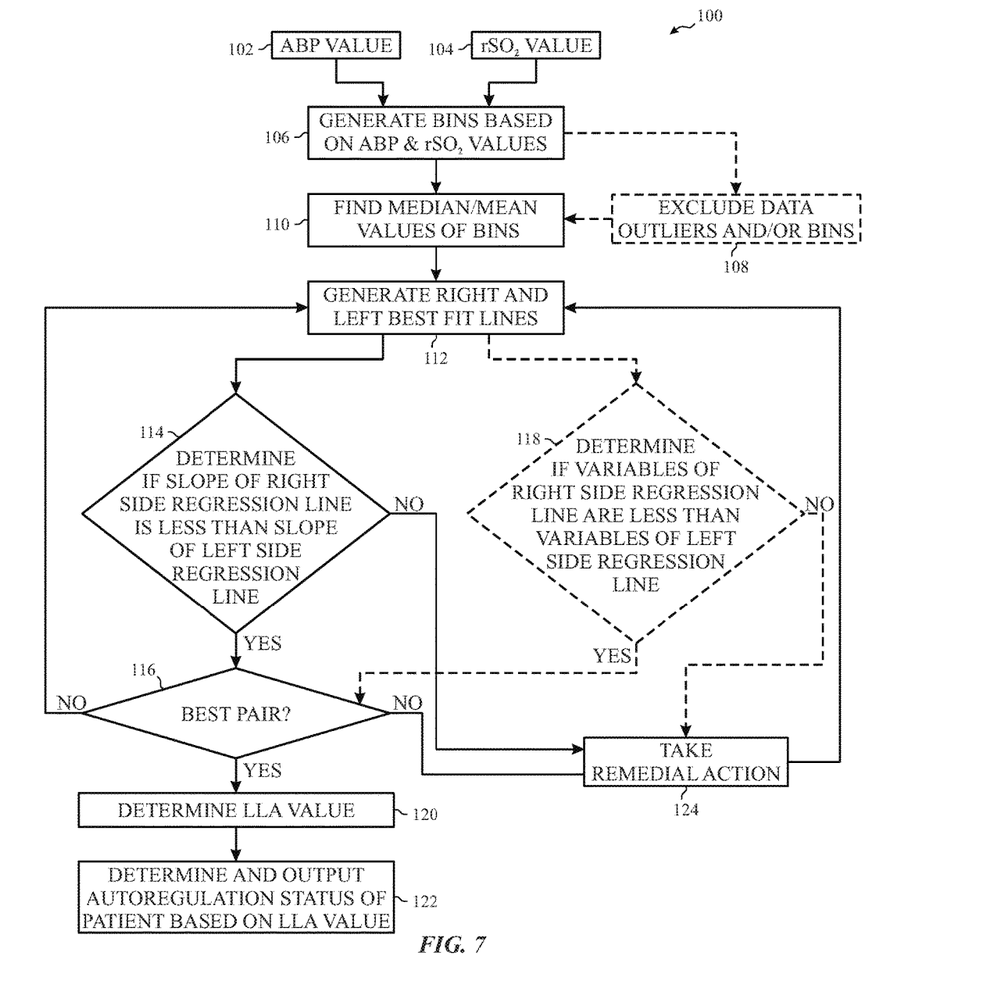
FIG. 7 is an embodiment of a process flow diagram of a method of monitoring autoregulation by reliably determining a LLA value.

FIG. 7 is a process flow diagram of a method 100 of monitoring autoregulation by reliably determining a LLA value 58, in accordance with an embodiment. Some or all of the steps of the method 100 may be implemented by the controller 16 (e.g., the processor 24 of the controller 16) of FIG. 1, for example, to determine whether the patient's autoregulation is impaired and/or to take an appropriate remedial action. In step 102 and step 104, the controller 16 may receive one or more physiological values, such as, for example, the blood pressure value 48 (e.g., arterial blood pressure value) and the oxygen saturation value 44 from the blood pressure sensor 12 and/or the oxygen saturation sensor 14. In step 106, the controller 16 generate a plurality of bins 82 for the oxygen saturation measurements 54 based on the blood pressure measurements 56 at each corresponding time point from the analysis window 50. As noted above, each bin 82 may include or represent a number of original measurements that fall within a particular interval or width 84, in order to reduce the effects of minor observations and/or measurements. In certain embodiments, the method 100 includes a step 108 where the controller 16 excludes or ignores data outliers 72, 74 (e.g., measurements indicative of signal noise) that are less than a pre-determined threshold. For example, in some situations, the controller 16 may exclude one or more measurements and/or one or more bins 86 that are less than a predefined threshold. In step 110, based on the remaining measurements and/or bins 82, the controller 16 may be configured to calculate a median and/or mean value of the bins 82. In step 112, based on the mean and/or mean value of the bins 82, the controller 16 may generate one or more regression lines or one or more pairs of regression lines, such as a pair of regression lines including one left side regression line 62 and one right side regression line 64. In certain embodiments, it may be beneficial to determine the most suitable pair of regression lines, so that the LLA value determined may be a reliable indication of the patient's autoregulation status.

In certain embodiments, the controller 16 may be configured to determine the most suitable pair of regression lines by determining if the slope of the right side regression line 64 (negative or flat slope) is less than the slope of the left side regression line 62 (positive slope). As noted above, the LLA value 58 may be the point or value on the $rSO_2$ curve 60 where the slope transitions from a positive slope to a flat or negative slope. Accordingly, the controller 16 may be configured to evaluate the slope of each pair of regression lines to find the best pair of regression lines (step 116). Specifically, the controller 16 may be configured to iteratively determine the best or most suitable pair of regression lines by identifying or minimizing the slope of the right side regression line 64 when compared to the slope of the left side regression line 62. For example, the controller 16 may compare the evaluation of each pair of regression lines with the evaluation of a previous pair of regression lines to algorithmically determine the most suitable or best pair of regression lines.

In certain embodiments of the method 100, in step 118, the controller 16 may be configured to determine the most suitable pair of regression lines by determining if the sum of the p-values of the right side regression line 64 and the p-value of the left side regression line 62 is less than the sum of the p-values of another pair of regression lines. As noted above, the p-value may be a significance value associated with the linear correlation of the blood pressure measurements 56 and the oxygen saturation measurements 54. In yet other embodiments of the method 100, in step 118, the controller 16 may be configured to determine the most suitable pair of regression lines by determining if various correlation coefficients of the right side regression line 64 are less than the correlation coefficients of the left side regression line 62. In certain embodiments, correlation coefficients may be utilized to indicate positive correlations, negative correlations, or the absence of correlations between the blood pressure measurements 56 and the oxygen saturation measurements 54. For example, a correlation coefficient may be between −1 and 1, inclusive, where −1 represents total negative correlation, +1 represents total positive correlation, and 0 represents the absence of correlation between the blood pressure measurements 56 and the oxygen saturation measurements 54. Accordingly, the controller 16 may be configured to evaluate various variables of each pair of regression lines to find the best pair of regression lines (step 116). Specifically, the controller 16 may be configured to iteratively determine the best or most suitable pair of regression lines by identifying or minimizing the p-value and/or various correlation coefficients of the right side regression line 64 when compared to the left side regression line 62.

In step 120, the controller 16 may determine the LLA value based on the best or most suitable pair of regression lines determined in step 116. Accordingly, in this manner, the controller 16 may optimize the determination of the LLA value 58 on the rSO$_2$ curve 60. Based on the determined best pair of regression lines, the LLA value 58 and/or the associated autoregulation status of the patient is output to the output device 18 in step 112, as further described with respect to FIG. 8. Further, the controller 16 may continue to monitor the patient's autoregulation status by continuing to receive physiological values (steps 102 and 104). If a best pair of regression lines is not found in step 116 or if the analysis of the regression lines fails (steps 114 and 118), the controller 16 may take appropriate remedial action in step 124. For example, the controller 16 may discard the determined regression lines, may not provide the LLA value to the output device 18, and may determine a new pair of regression lines and/or may obtain new physiological values. In some cases, the controller 16 may cause the output device 18 to display a blank display screen or provide an appropriate visual or audible indication that the patient's autoregulation status is unavailable.

Figure 8:
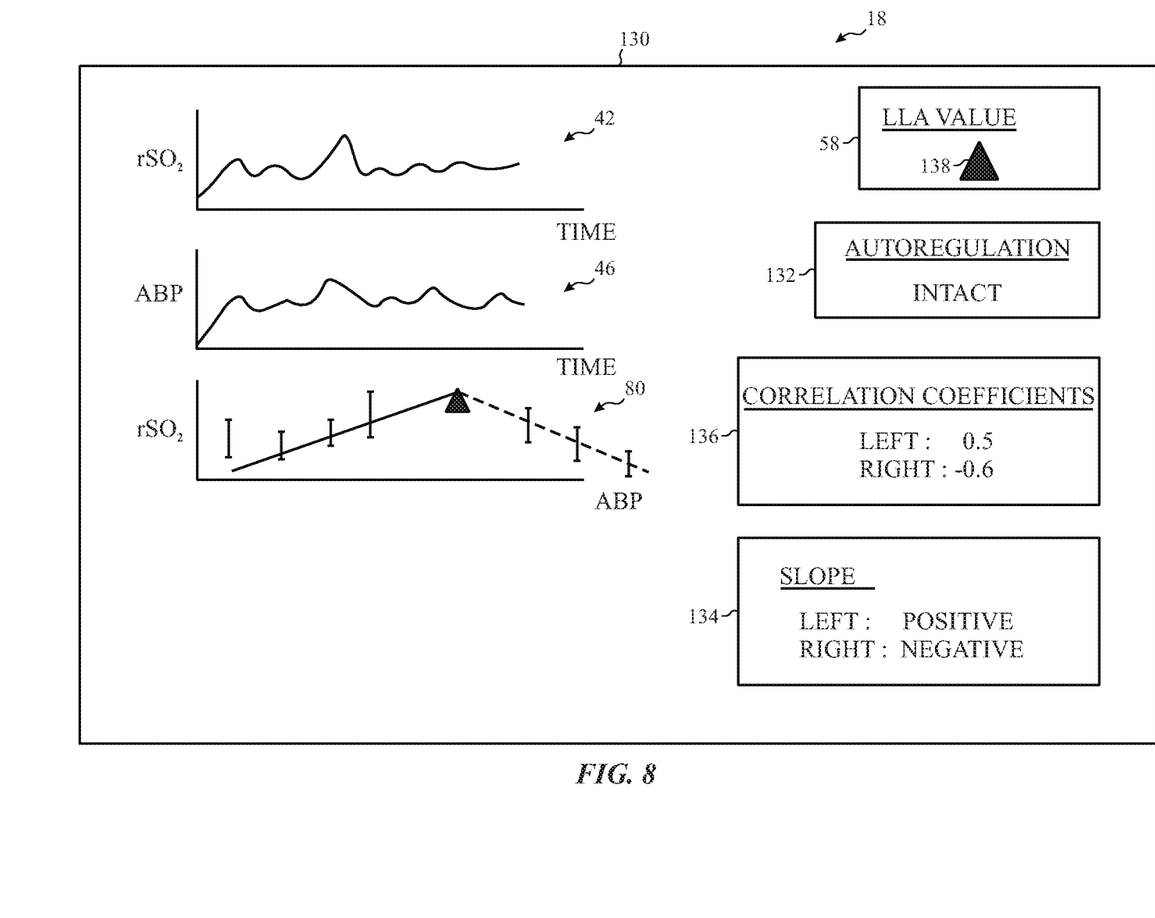
FIG. 8 is an embodiment of a display configured to display various information related to monitoring the autoregulation of a patient.

FIG. 8 is an embodiment of a display 130 of the output device 18 that is configured to display various information related to monitoring the autoregulation of a patient. As illustrated in FIG. 8, various types of information may be displayed on the display 130, including graphs related to the oxygen saturation value 44 (e.g., regional oxygen saturation value, rSO$_2$, etc.) or the blood pressure value 46 obtained from the patient over the period of time 40 from the regional oxygen saturation sensor 14 or the blood pressure sensor 12, as illustrated in FIGS. 2A-2B. In addition, the display 130 may include graphs depicting linear correlations between the oxygen saturation measurements 54 plotted against the blood pressure measurements 56 (e.g., the rSO$_2$ curve 60), as illustrated in FIGS. 3-4. In addition, the display 130 may include graphs related to regression lines between the oxygen saturation measurements 54 and the blood pressure measurements 56 generated by binning measurements and calculating mean/median values associated with the bins 82, as illustrated in FIGS. 5-6. Further, in certain embodiments, the display 130 may display various other types of information, such as an autoregulation status 132, various correlation coefficients 136, a slope 134, and/or the LLA value 58. In certain embodiments, the LLA value 58 may additionally be depicted on one or more graphs illustrated on the display 130 via one or more visual identifiers 138 (e.g., symbols, arrows, marks, indicators, etc.). Indeed, other types of graphical information (e.g., data outliers 72, 74) may also be displayed on the graphs on the display 130.

While the disclosure may be susceptible to various modifications and alternative forms, specific embodiments have been shown by way of example in the drawings and have been described in detail herein. However, it should be understood that the embodiments provided herein are not intended to be limited to the particular forms disclosed. Rather, the various embodiments may cover all modifications, equivalents, and alternatives falling within the spirit and scope of the disclosure as defined by the following appended claims. Further, it should be understood that certain elements of the disclosed embodiments may be combined or exchanged with one another.

What is claimed is:

1. A method for monitoring autoregulation of a patient, the method comprising:
   receiving, by a processor and from one or more sensors, a blood pressure signal indicative of a blood pressure of a patient and a regional oxygen saturation signal indicative of blood oxygen saturation of the patient;
   determining, by the processor, one or more pairs of linear correlation lines between the blood pressure signal and the regional oxygen saturation signal based on one or more bins, wherein each of the one or more bins comprises one or more regional oxygen saturation values derived from the regional oxygen saturation signal;
   determining, by the processor, a value indicative of the patient's autoregulation status based on a first pair of linear correlation lines selected from the one or more pairs of linear correlation lines; and
   at least one of:
      presenting, via a display, information indicative of the patient's autoregulation status; or
      outputting, via an audio device, information indicative of the patient's autoregulation status,
      wherein the information indicative of the patient's autoregulation status is based on the value indicative of the patient's autoregulation status.

2. The method of claim 1, comprising generating the one or more bins by grouping one or more regional oxygen saturation values based on one or more blood pressure values derived from the blood pressure signal.

3. The method of claim 1, comprising generating a mean value or a median value of the one or more bins.

4. The method of claim 3, comprising determining the one or more pairs of linear correlation lines based the mean value or the median value.

5. The method of claim 4, wherein each pair of the one or more pairs of linear correlation lines comprises a left side regression line and a right side regression line.

6. The method of claim 5, comprising minimizing a first slope of the right side regression line when compared to a second slope of the left side regression line to select the first pair of linear correlation lines and determine the value indicative of the patient's autoregulation status.

7. The method of claim 5, comprising minimizing a first p-value or a first correlation coefficient of the right side regression line when compared to a second p-value or a second correlation coefficient of the left side regression line to select the first pair of linear correlation lines and determine the value indicative of the patient's autoregulation status.

8. The method of claim 1, wherein determining the value indicative of the patient's autoregulation status comprises determining an upper autoregulation limit or a lower autoregulation limit of the first pair of linear correlation lines.

9. The method of claim 1, comprising excluding one or more regional oxygen saturation values from the one or more bins prior to determining the one or more pairs of linear correlation lines.

10. The method of claim 1, wherein determining the one or more pairs of linear correlation lines comprises excluding one or more bins prior to selecting the first pair of linear correlation lines and determining a value indicative of the patient's autoregulation status.

11. A monitor for monitoring autoregulation of a patient, the monitor comprising:
a memory storing instructions for:
receiving a blood pressure signal indicative of a blood pressure of a patient and a regional oxygen saturation signal indicative of blood oxygen saturation of the patient;
determining one or more pairs of linear correlation lines between the blood pressure signal and the regional oxygen saturation signal based on one or more bins, wherein each of the one or more bins comprises one or more regional oxygen saturation values derived from the regional oxygen saturation signal;
determining a value indicative of the patient's autoregulation status based on a first pair of linear correlation lines selected from the one or more pairs of linear correlation lines; and
at least one of:
presenting, via a display, information indicative of the patient's autoregulation status; or
outputting, via an audio device, information indicative of the patient's autoregulation status,
wherein the information indicative of the patient's autoregulation status is based on the value indicative of the patient's autoregulation status; and
a processor configured to execute the instructions.

12. The monitor of claim 11, wherein the memory stores instructions for generating the one or more bins by grouping one or more regional oxygen saturation values based on one or more blood pressure values derived from the blood pressure signal.

13. The monitor of claim 11, wherein the memory stores instructions for generating a mean value or a median value of the one or more bins, and determining the one or more pairs of linear correlation lines based the mean value or the median value.

14. A system, comprising:
a regional oxygen saturation sensor configured to generate an oxygen saturation signal indicative of blood oxygen saturation of a patient; and
a monitor, comprising:
a display; and
a processor configured to:
receive a blood pressure signal indicative of a blood pressure of the patient and the oxygen saturation signal;
determine one or more pairs of linear correlation lines between the blood pressure signal and the oxygen saturation signal based on one or more bins, wherein each of the one or more bins comprises one or more regional oxygen saturation values derived from the oxygen saturation signal;
determine a value indicative of the patient's autoregulation status based on a first pair of linear correlation lines selected from the one or more pairs of linear correlation lines; and
at least one of:
present, via the display, information indicative of the patient's autoregulation status; or
output, via an audio device, information indicative of the patient's autoregulation status,
wherein the information indicative of the patient's autoregulation status is based on the value indicative of the patient's autoregulation status.

15. The system of claim 14, wherein the regional oxygen saturation sensor is further configured to generate the blood pressure signal.

16. The system of claim 14, wherein the processor is configured to present the information indicative of the patient's autoregulation status by at least presenting the value indicative of the patient's autoregulation status on the display.

17. The system of claim 14, wherein the processor is configured to cause display of a visual indication of a lower autoregulation limit or an upper autoregulation limit, a slope of the linear correlation, a correlation coefficient, or any combination thereof on the display.

18. The system of claim 14, wherein the processor is configured to generate the one or more bins by at least grouping one or more regional oxygen saturation values based on one or more blood pressure values derived from the blood pressure signal.

19. The system of claim 14, wherein the processor is configured to generate a mean value or a median value of the one or more bins, and determine the one or more pairs of linear correlation lines based the mean value or the median value.

20. The system of claim 19, wherein the processor is configured to select the first pair of linear correlation lines from the one or more pairs of linear correlation lines based on one or more slopes of the one or more pairs of linear correlation lines.

21. The system of claim 14, wherein the processor is configured to exclude one or more regional oxygen saturation values from the one or more bins or exclude one or more bins when determining the one or more pairs of linear correlation lines.

* * * * *